United States Patent [19]

Garner-Gray et al.

[11] Patent Number: 5,336,665

[45] Date of Patent: Aug. 9, 1994

[54] PERFUME PARTICLES

[75] Inventors: Peter F. Garner-Gray, Preston; Alexander Martin, Warrington; John R. Martin, Birkenhead; Maurice Webb, Chester, all of England

[73] Assignee: Lever Brothers Company, Division of Conopco, Inc., New York, N.Y.

[21] Appl. No.: 104,391

[22] Filed: Aug. 9, 1993

Related U.S. Application Data

[63] Continuation of Ser. No. 955,077, Oct. 1, 1992, abandoned.

[30] Foreign Application Priority Data

Oct. 2, 1991 [GB] United Kingdom ............ 9120951.0

[51] Int. Cl.$^5$ .................. B01J 13/06; C11D 17/00
[52] U.S. Cl. .......................... 512/4; 252/8.6; 252/174.11; 252/174.13; 428/402; 424/401; 424/489; 424/490
[58] Field of Search ............ 512/4; 252/8.6, 174.11, 252/174.13; 428/402; 424/401, 489, 490

[56] References Cited

U.S. PATENT DOCUMENTS

| | | | |
|---|---|---|---|
| 3,436,225 | 4/1969 | Raible | 99/48 |
| 3,449,266 | 6/1969 | Cashman | 252/522 |
| 4,212,759 | 7/1980 | Young et al. | 252/119 |
| 4,954,285 | 9/1990 | Wierenga et al. | 252/174.11 |
| 4,973,422 | 11/1990 | Schmidt | 252/174.11 |
| 5,011,690 | 4/1991 | Garvey et al. | 424/401 |
| 5,078,904 | 1/1992 | Behan et al. | 252/8.6 |
| 5,112,688 | 3/1992 | Michael | 428/402.2 |

FOREIGN PATENT DOCUMENTS

| | | |
|---|---|---|
| 0332259 | 9/1989 | European Pat. Off. |
| 0332260 | 9/1989 | European Pat. Off. |
| 1408422 | 8/1964 | France . |
| 1558480 | 12/1967 | France . |
| 1306924 | 2/1973 | United Kingdom . |
| 1374105 | 11/1974 | United Kingdom . |
| 1570608 | 7/1980 | United Kingdom . |
| 2066839 | 7/1981 | United Kingdom . |

OTHER PUBLICATIONS

European Search Report & Annex, EP 92-30-8932, Feb. 1993.

Copending appl'n: Garner-Gray et al. –S/N 07/955,210, filed Oct. 1, 1992.

Primary Examiner—Arthur C. Prescott
Attorney, Agent, or Firm—A. Kate Huffman

[57] ABSTRACT

A hydrophobic porous inorganic carrier particle having at least a pore volume of 0.1 ml/g consisting of pores with a diameter of 7 to 50 Å and having a perfume absorbed into said particle. The invention also comprises a detergent composition containing the carrier particle and a method of manufacturing the carrier particle.

7 Claims, No Drawings

PERFUME PARTICLES

This is a continuation, application of Ser. No. 07/955,077, filed Oct. 1, 1992, now abandoned.

This invention relates to perfume particles and in particular to perfume particles adapted for use in laundry detergent or bleaching compositions, fabric softener compositions—especially dryer activated solid softener compositions or antiperspirant or deodorant compositions. The particles allow the intensity of perfume in a composition to be controlled, suppress unwanted perfume loss and can act as a delivery means to fabric, skin or other article.

Perfumes are used in compositions for two main reasons. The first is to disguise any chemical odours of the base ingredients and the second is to provide a pleasing odour to the article treated with the composition. Normally, one perfume performs both functions. Perfumes are often added directly to laundry compositions e.g. by spraying onto granular compositions. However, perfumes are, in general, volatile and many perfume ingredients can be lost from the product during processing or storage, or destroyed or damaged by contact with the highly alkaline conditions present in laundry compositions or by contact with some components of the composition (e.g. bleaches, enzymes), or by contact with the acidic conditions present in deodorant compositions. Perfumes are also lost from the composition to aqueous environments such as the wash liquor thereby reducing the potential level of perfume deposited on the fabric. Another example of loss occurs in soap or non-soap detergent bar manufacture where the perfume is added to a hot, aqueous paste which is then dried to form bars. High temperatures such as those encountered in the tumble drier can also lead to unwanted loss. There is therefore a need for a carrier that will suppress unwanted perfume loss, reduce degradation and give enhanced delivery of perfume to the fabric, skin or other article.

A further disadvantage that arises from the direct addition of perfumes to compositions is that the same perfume must be used to perfume both the composition and the article to which it is delivered. There is no flexibility for example to allow a laundry composition to have one perfume and the cleaned fabric another perfume.

Another problem arises from the trend towards more concentrated products mainly for environmental reasons, for example high bulk density laundry detergent compositions, highly concentrated fabric softening compositions and solid deodorant sticks. These concentrated products are either used at lower dosage levels by the consumer or are diluted to make up the "normal" dose level. In order to ensure that these concentrated products give the same or a greater level of perfume delivery to fabric, liquor or skin it is necessary to include the perfume at appropriately higher levels. This can lead to concentrated products having unacceptably heavy odours which are unattractive to the consumer. There is thus a need to control the intensity of the perfume in a composition, so that unacceptably heavy odours can be avoided.

In the past, attempts at solving the problem of unwanted loss or degradation of perfume have centred around the use of carriers impregnated with the perfume. For example EP 0 332 259A (Procter and Gamble/Sagel) discloses certain perfume particles formed by adsorbing a perfume onto silica. EP 0 332 260A (Procter and Gamble/Ladd) discloses the use of such particles in fabric softening compositions. In this prior art there is much emphasis on particle size, total pore volume and surface area of the silica since adsorption capacity is of prime importance. These alleged solutions, however, do not sufficiently overcome the problem of perfume loss, unacceptable intensity or inflexibility since the perfume is not captured by the carrier.

It is known from GB 1 570 608 (Doulton/Parkes) that ceramics of pore size less than 5 microns can be impregnated with a perfume to form an air freshener.

It is also known from J53/26335 (Seiwa Sangyo KK/Yasunaga) to absorb perfume on a granular powder which can be silica gel to form perfumed accessories such as necklaces or air fresheners. The one example discloses a perfumed Type B silica gel with a surface area of 350 $m^2/g$.

We have now found that the disadvantages of the prior art can be overcome, perfume intensity controlled, unwanted loss suppressed and delivery enhanced if the carrier is hydrophobic and has a minimum pore volume comprising pores of a certain size range.

Accordingly a first aspect of the invention provides a hydrophobic porous inorganic carrier particle having at least a pore volume of 0.1 ml/g consisting of pores with a diameter of 7 to 50 Å and having a perfume absorbed into said particle.

As used herein, hydrophobic carrier particle means a particle which passes a hydrophobicity test as hereinafter defined. The test is based on measuring the percentage of a perfume oil recovered from a perfumed carrier particle placed in salt solution. Hydrophobic particles tend not to release oil to the salt solution and typically have percentage recovery values of less than 5%. The test comprises adding 0.1 g of citral to 0.6 g of inorganic carrier with stirring until all of the perfume is absorbed. The particles are then allowed to equilibrate overnight in a sealed vial. The perfumed particles are then added to 5 ml of a 5% by weight $K_2CO_3$ solution of pH 10 and left to stand for 5 minutes at room temperature. 5 ml of hexane are then added to the salt solution with gentle stirring. 1 ml of the hexane is extracted and the concentration of citral in the hexane determined by UV analysis. The % recovery can then be calculated. Preferably, hydrophobic particles have percentage recovery values of less than 20%. For non-silica particles, such as Alumina, it may be necessary to add 20 to 25 ml of IPA to the $K_2CO_3$ solution in order to assist with the wetting of the particles.

The carrier particles are used to make perfumed compositions such as dry flowable detergent compositions, laundry bars, fabric softener compositions and deodorant compositions in solid, liquid or aerosol form. Use of the carrier particle can allow reduced levels of perfume to be added to the composition since unwanted loss is mitigated, can control the intensity of perfume in concentrated compositions so that both composition and treated article carry acceptable levels of perfume and can allow the composition and the article treated therewith to carry different perfumes and can give enhanced delivery of perfume to treated articles.

The perfume can be sprayed onto the inorganic carrier in various ways well known in the art. It can be added neat or with diluents, viscosity modifiers or wetting agents and may be absorbed at room temperature or at elevated temperatures or may be vacuum filled. As used herein the term "perfume" denotes one or a mixture of perfumed components, optionally mixed with a suitable solvent, diluent or carrier. Perfume components and mixtures thereof which can be used for the preparation of such perfumes may be natural products such as essential oils, absolutes, resinoids, resins, concretes, etc., and synthetic perfume components such as hydrocarbons, alcohols, aldehydes, ketones, ethers, acids, esters, acetals, ketals, nitriles etc., including saturated and unsaturated compounds, aliphatic, carbocyclic and heterocyclic compounds. Examples of such perfume components are: geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol acetate, 2-phenylethanol, 2-phenylethyl acetate, benzyl alcohol, benzyl acetate, benzyl salicylate, benzyl benzoate, styrallyl acetate, amyl salicylate, dimethylbenzylcarbinol, trichloro-methylphenycarbinyl acetate, p-tert.butylcyclohexyl acetate, isononyl acetate, vetiveryl acetate, vetiverol, alpha-n-amylcinammic aidehyde, alpha-hexylcinammic aidehyde, 2-methyl-3-(p-tert.butylphenyl)propanal, 2-methyl-3-(p-isopropylphenyl)propanal, 3-(p-tert.butylphenyl)propanal, tricyclodecenyl acetate, tricyclodecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy-3-pentyltetrahydropyran, methyl dihydrojasmonate, 2-n-heptlcyclopentanone, 3-methyl-2-pentylcyclopentanone, n-decanal, n-dodecanal, 9-decenol-1, phenoxyethyl isobutyrate, phenylacetaldehyde dimethyl acetal, phenylacetaldehyde diethyl acetal, geranonitrile, citronellonitrile, cedryl acetate, 3-isocamphylcyclohexanol, cedryl methyl ether, isolongifolanone, aubepine nitrile, aubepine, heliotropine, coumarin, eugenol, vanillin, diphenyl oxide, hydroxycitronellan, ionones, methyl ionones, isomethyl ionones, irones, cis-3-hexenol and esters thereof, indane musk fragrances, tetralin musk fragrances, isochroman musk fragrances, macrocyclic ketones, macrolactine musk fragrances, ethylene brassylate, aromatic nitromusk fragrances.

Suitable solvents, diluents or carriers for perfumes as mentioned above are for example: ethanol, isopropanol, diethylene glycol monoethyl ether, dipropylene glycol, diethyl phthalate, triethyl citrate etc.

For certain applications, the perfume compositions are substantive to maximise the effect on fabric, skin etc. A substantive fragrance is one which contains a sufficient percentage of substantive fragrance materials that when the fragrance is used at normal levels it deposits a desired odour on the fabric or skin. The perfumes may also be deodorant perfumes, anti-microbial perfumes or have other functionalities desirable for certain applications. Examples are disclosed in GB 1 566 538, GB 1 572 949, EP 62368, EP 49543 EP 3171, EP 1 471 191, EP 430 315 and EP 91200560 (all in the name of Unilever) incorporated herein by reference.

The hydrophobic perfume particles preferably release perfume once they are attached to fabrics, skin etc. The particles can be applied to fabrics either from a wash, rinse liquor or in the dryer or by direct application from a laundry bar or to the skin or hair from a deodorant stick or aerosol, shampoo or soap bar.

Suitable inorganic carriers for use in the present invention include aluminosilicates such as certain zeolites, clays, aluminas and silicas all with pore volume of at least 0.1 ml/g consisting of pores with a diameter between 7 and 50 Å which either have been thermally or chemically treated to render them hydrophobic or which by their nature are hydrophobic, such as high silica zeolites. Thermal treatment has been found to be preferred because the degree of hydrophobicity can be more easily kept to the level required for effective perfume delivery.

Preferably the inorganic carrier has a pore volume of at least 0.2 ml/g, most preferably between 0.1 ml/g and 1.5 ml/g consisting of pores with diameter of between 7 and 50 Å.

We have also found that when the perfumed carrier has a pore volume of at least 0.1 ml/g consisting of pores with a diameter between 7 and 50 Å the carrier can also function as a malodour absorber. Preferably the carrier has a pore volume of at least 0.1 ml/g consisting of pores with diameters between 20 and 40 Å.

The treatment can comprise heating the inorganic carrier at a temperature between 500° C. and 1000° C. for up to 3 hours. Precise temperatures and times are determined by the particular carrier used. Preferably the inorganic carrier has a particle size of greater than 1 micron, more preferably greater than 5 microns, most preferably between 1 and 500 microns. In the context of the present invention particles sizes are determined by sieving, particle sizes below 100 microns are determined by a Malvern 3600 particle analyser. Chemical hydrophobing can be achieved by use of a reactive silane treatment.

The particles of the present invention can also be formed into aggregates of two or more particles to make aggregates of several particle diameters, for example 1000 $\mu$m.

Although the inorganic carrier has a pore volume of preferably 0.1 ml/g to 1.5 ml/g consisting of pores with a diameter of between 7 and 50 Å, the total pore volume of the carrier can be greater and include pores with a diameter greater than 50 Å. For example the total pore volume can be between 0.2 ml/g and 2.5 ml/g.

In the context of the present invention the porosity characteristics of the carrier are determined by nitrogen adsorption isotherm. The volume, $V_a$, of nitrogen adsorbed in pores with diameters between 17 Å and 50 Å is determined according to the method of Barrett, Joynet and Halenda, JACS 73 373 (1951), from the absorption data. The volume, $V_b$, of nitrogen absorbed in pores of between 7 Å and 20 Å in diameter is determined using T-plot analysis according to the method of Lippons and deBoer, J Catalysis 4 319 (1965). $V_b$ is calculated from the intercept at $t=0$ of a line fitted to the linear portion of the t-plot curve within the range, $t=3$ to $t=16$ Å. If, within this range, there are two linear regions, the line with the lower gradient is used. If there are three linear regions the line is fitted to the one giving the lowest intercept at $t=0$. Inorganic carriers suitable for use in the present invention have a volume of $V_a$ plus $V_b$ greater than 0.1 ml/g.

Inorganic carriers suitable for treating for use in the present invention include silicas such as Gasil 200 also referred to as Gasil ex Crosfield Chemicals with a volume $V_a+V_b$ of 0.64 ml/g, an average particle size of 10–15 microns and a surface area of 730 m$^2$/g; Sorbsil ex Crosfield Chemicals with a volume $V_a+V_b$ of 0.69 ml/g, average particle size of 50–250 microns, and surface area of 730 m$^2$/g; Sorbsil C30 ex Crosfield Chem. with a volume of $V_a+V_b$ of 0.98 ml/g particle size of 60 microns, and surface area of 640 m$^2$/g and a conventional sodium zeolite Y ex Conteka with a volume $V_a+V_b$ of 0.37 ml/g, particle size of 5 microns and surface area of 690 m²/g and MD 263 a silica as described in Example 3 of EPO 287 232 with a volume Va+Vb of 0.28 ml/g, a surface area of 730 m²/g and a particle size of 25–30 microns, all of which can be treated to render them hydrophobic.

The perfumes absorbed into the carrier are preferably added at levels below the theoretical maximum absorption capacity of the carrier. For an "unperfumed" composition or low perfume intensity composition the perfume absorbed into the carrier is added at levels below the absorption capacity of the pore volume consisting of pores having a pore diameter of 7 to 50 Å. For a composition that is perfumed differently from the article treated therewith, the perfume intended to be delivered to the article is first absorbed into the carrier at a level below the absorption capacity of the pore volume consisting of pores having a pore diameter of 7 to 50 Å. The perfume intended for the composition may then be either absorbed by the carrier up to the level of its maximum capacity or by the composition. Preferably the ratio by weight of carrier to perfume is less than 25:1, more preferably between 12:1 and 3:1 e.g. 10:1 or 6:1. The level of addition of perfume should be chosen to give free flowing particles.

A second aspect of the invention relates to the use of perfumed inorganic carrier particles in detergent compositions. Such compositions typically comprise detersive surfactants and/or detergency builders, bleaches and, optionally, additional ingredients such as enzymes, fabric brighteners, fabric softeners and the like.

Accordingly a second aspect of the invention provides a detergent composition comprising at least one surfactant and from 0.1% to 60% by weight of a hydrophobic porous inorganic carrier particle having a pore volume of at least 0.1 ml/g consisting of pores with a diameter of 7 to 50 Å and having a perfume absorbed into said particle.

Surfactants useful in the detergent compositions herein include well-known anionic, nonionic, amphoteric and zwitterionic surfactants. Typical of these are the alkyl benzene sulphonates, alkyl sulphonates, allyl- and alkyl ether sulphates, primary alkyl sulphates, alkoxylated alcohols, alpha-sulphonates of fatty acids and of fatty acid esters, alkyl betaines, polyalkyl glycosides and the like all known in the detergent art. The surfactant is preferably present at a level from 5% to 60% by weight, more preferably 10% to 50%.

Useful detergency builders for the detergent compositions herein include any of the conventional inorganic and organic water soluble builder salts as well as the various insoluble salts. Examples are alkali metal carbonates, borates, phosphates, polyphosphates, tripolyphosphates, bicarbonates, silicates, sulphates, calcite seeded carbonates and zeolites such as zeolite 4A and citric acid salts. The builder is preferably present at a level between 5 and 80% by weight, more preferably 10 and 60% by weight.

Useful bleaches include halogen bleaches, peroxyacids such as diperoxydodecanedioic acid, or bleach systems that comprise a peroxide compound which liberates hydrogen peroxide in aqueous solution and an activator. Hydrogen peroxide sources are well known in the art, and include compounds such as alkali metal perborates, percarbonates, persulphates and persilicates, and urea peroxide and the like; particularly percarbonate.

Activators such as are described in GB 836,988, GB 855,735, GB 907,356, GB 907,358, GB 970,950, GB 1,003,310, GB 1,246,339, U.S. Pat. No. 3,332,882, U.S. Pat. No. 4,128,494, CA 844,481, and ZA 68/6344 are preferred. Particularly preferred are N,N,N,N-Tetraacetylethylenediamine (TAED), 1,2,3,4,6-Pentaacetylglucose (GPA), Sodium-p-acetoxybenzenesulphonate (SABS), Sodium-p-benzoyloxybenzenesulphonate (SBOBS), Sodium-p-nonanoyloxybenzenesulphonate (SNOBS), Sodium-p-3,5,5-trimethylhexanoyloxy-benzenesulphonate (iso-SNOBS), 2-N, N,N-Trimethylammonioethyl-4-sulphophenylcarbonate (CSPC), 2-N,N,N-Trimethylammoniopropionitrile tosylate (TAP), and transition metal catalysts.

As optional ingredients the detergent compositions can comprise additional perfume carriers.

A third aspect of the invention relates to the use of perfumed inorganic carrier particles in fabric softener compositions. Such fabric softener compositions are particularly those which are attached to substrates for use in laundry dryers.

Accordingly a third aspect of the invention provides a dryer activated fabric softener composition comprising a fabric softener and a hydrophobic porous inorganic carrier particle having a pore volume of at least 0.1 ml/g consisting of pores with a diameter of 7 to 50 Å and having a perfume absorbed into said particle.

The fabric softener is typically cationic and usually a quaternary ammonium salt of formula $[R_1R_2R_3R_4N^+]Y^-$ wherein one or two of the R groups is an aliphatic radical or an alkylphenyl or alkylbenzyl radical having from 10 to 20 carbon atoms in the chain. The remaining R groups being selected from $C_1$–$C_4$ alkyl and $C_2$–$C_4$ hydroxyalkyl. Preferably the hydrophobic R groups are attached to the N atom via one or more ester links. The quaternary ammonium compounds useful herein also comprise imidazolinium compounds. Y is typically a halide, nitrate, bisulphate, ethylsulphate or methyl sulphate.

The fabric softening compositions of the invention preferably comprise from 5% to 80% by weight of fabric softener, more preferably from 5% to 50%. The compositions also preferably comprise from 1% to 60% of the perfumed inorganic carrier particles.

The fabric softening compositions may also contain various optional ingredients including auxiliary softeners, soil release agents, brighteners etc.

Another aspect of the present invention relates to deodorant compositions comprising inorganic carrier particles having at least a pore volume of 0.1 ml/g consisting of pores with a diameter of 7 to 50 Å and having a perfume absorbed into said particle.

Typically deodorant compositions comprise ingredients determined by the nature and form of the finished product.

Examples of these ingredients which are optionally present include:
antiperspirant materials, such as aluminium and/or zirconium salts;
cosmetically acceptable vehicles such as straight chain and branched alcohols, for example ethanol, isopropanol or isobutanol;
deodorants and deodorant levels of metal salts;
volatile and non-volatile silicones, such as the Dow Corning dimethyl cyclosiloxane fluids DC344 and DC345, and polydimethyl siloxane having a viscosity in excess of 5 $mm^2s^{-1}$, for example from 5 to 100 $mm^2s^{-1}$ such as Dow Corning 200 fluids;
thickeners such as clays and silicas;
humectants such as polyols, for example glycerol;

emollients;
skin feel improvers such as talc and finely divided polyethylene e.g. ACUMIST B18;
gelling agents such as stearyl alcohol, or waxes such as castor wax;
preservatives and antioxidants; and
other cosmetic adjuncts conventionally employed in stick, roll-on lotion, liquid spray, cream, and propellant-driven aerosol products.

Products for topical application comprise 1 to 25% by weight of the carriers according to the invention.

The particle can be encapsulated in a coating which is soluble or disrupted by heat, pH change, pressure and other known coating disruption techniques. The following non-limiting examples illustrate the compositions of the present invention.

Example 1

The perfumed hydrophobic inorganic carrier particles hereinafter described were made by heating the inorganic carrier at a temperature between 1000° C. and 500° C. for up to 3 hours followed by adding an appropriate amount of perfume dropwise, with stirring to a jar containing the carrier. The jar was then sealed and allowed to equilibrate overnight.

The extent to which the perfumed inorganic carrier particles suppress the loss of perfume from the carrier was assessed by measuring the equilibrium vapour pressure of perfume above a given particle compared to that above free perfume. This then allows a calculation of the percentage reduction in vapour pressure and thus allows a quantitative comparison between different carriers.

The apparatus used comprised a two-necked, 500 ml flask in a thermostated water bath. One neck of the flask was connected via a short flexible connection to a water manometer (glass, 2 mm internal bore). The other neck was fitted with a dropping funnel to allow samples to be placed in the flask. The system was stabilised at 65° C. with the tap of the dropping funnel in the open position. The vapour pressure above a free perfume sample was measured by introducing the perfume via the funnel, closing the tap and noting the manometer reading once a steady state has been reached. For particulate samples the same procedure was followed except that the solid was introduced using a filter funnel which was then immediately replaced with the dropping funnel to seal the flask.

| Particle | Thermal Treatment | $V_a + V_b$ ml/g | Vapour Pressure at 65° C. | % Recovery in Hydrophobicity test |
|---|---|---|---|---|
| A Gasil 200[1] | 800° C./2 hrs | 0.3 | 11 | 2.6 |
| B Gasil 200 | 700° C./2 hrs | 0.37 | 15 | 1.7 |
| C Gasil 200 | None | 0.64 | 4 | 56.8 |
| D Sorbsil[2] | 700° C./2 hrs | 0.38 | 11 | 1.7 |
| E Sorbsil | 600° C./2 hrs | 0.43 | 8 | 3.7 |
| F Sorbsil | 550° C./2 hrs | 0.42 | 4 | 10.7 |
| G Sorbsil | None | 0.69 | 4 | 24.3 |
| H EP 10X[3] | 700° C./2 hrs | 0.04 | 24 | 39.8 |
| I EP 10X | None | 0.02 | 22 | 62.9 |
| Free perfume | — | — | 40 | — |

[1]Gasil 200 is a silica gel ex Crosfield Chemicals
[2]Sorbsil is a silica gel ex Crosfield Chemicals
[3]EP 10X is a silica gel ex Crosfield Chemicals All particles B to I had a carrier to perfume ratio of 6:1. Particle A has a carrier to perfume ratio of 7:1. The perfume used was amyl acetate.

These results show that perfumed inorganic carrier particles according to the invention are effective at suppressing perfume loss and that preferred thermal treatment of the carrier comprises heating the carrier at a temperature between 550° C. and 800° C. of 2 hours.

Example 2

0.056 g of a hydrophobic inorganic carrier particle from Example 1 perfumed with LP927LL ex Quest International Limited was mixed with 4 g of New System Persil Automatic ex Lever and added to 1l of demineralised water at 35° C. Terry cotton swatches were then added to the liquor in a tergotometer to give a liquor to cloth ratio of 20:1. The swatches were washed at a temperature of 45° C. for 15 minutes and rinsed for 5 minutes in cold water. The cloths were wrung out by hand and line dried. A perfume intensity score was determined for each cloth by a method of panel assessment in which each cloth is given an intensity score on a scale of 0 to 5, 5 being very strong.

| Particle | Hydrophobic | Perfume Intensity Score | | | | | |
|---|---|---|---|---|---|---|---|
| | | 1 | 2 | 3 | 4 | 5 | 6 |
| D | Yes | 2.85 | 2.35 | 3.07 | 2.84 | 2.79 | — |
| G | No | 0.92 | 0.63 | — | — | — | — |
| B | Yes | 2.02 | 1.55 | — | — | — | 1.56 |
| C | No | — | — | — | 0.29 | — | 0.50 |
| F | Yes | — | 1.22 | — | — | — | — |
| H | Yes | — | — | — | — | 0.56 | — |
| I | No | — | — | — | — | 0.54 | — |
| Free perfume | — | 0.60 | 0.65 | 0.29 | 0.29 | 0.50 | 0.61 |

These results show that perfumed hydrophobic inorganic carrier particles according to the invention are effective at enhancing delivery of perfume to fabrics. Compare for example particle D which is hydrophobic with particle G which is not or particle B which is hydrophobic with particle C which is not.

Example 3

Terry cotton swatches washed as in Example 2 were either line dried or tumble dried and the perfume intensity on the dried cloth assessed as in Example 2.

| Particle | Hydrophobic | Perfumed Intensity Score | | | |
|---|---|---|---|---|---|
| | | Line Dried | | Tumble Dried | |
| | | 1 | 2 | 1 | 2 |
| B | Yes | 1.2 | 1.94 | 1.99 | 2.74 |
| D | Yes | 1.77 | 2.57 | 0.92 | 2.03 |
| Free perfume | — | 0.35 | 0.40 | 0.67 | 0.57 |

These results show that the perfumed inorganic carrier particles according to the invention are effective at enhancing delivery of perfume to fabric and prevent unwanted loss of perfume in the tumble dryer.

Example 4

Perfumed hydrophobic inorganic carrier particles were made by heating the inorganic carrier particle at a temperature between 500° C. and 700° C. for up to 2 hours followed by adding an appropriate amount of perfume (LP927 LL ex Quest International Limited) drop-wise, with stirring to a jar containing the carrier. The jar was sealed and allowed to equilibrate overnight.

The extent to which these carriers enhance delivery to fabric was then tested as in Example 2.

| Particle | Thermal Treatment | Perfume Intensity Score |
|---|---|---|
| J Sorbsil[2] | 700° C./2 hrs | 2.27 |
| K Sorbsil | 600° C./1½ hrs | 1.65 |
| L Sorbsil | 500° C./1½ hrs | 0.74 |
| M Sorsbil | 500° C./1 hr | 0.63 |
| Free Perfume | — | 0.35 |

These results show that perfumed inorganic carrier particles according to the invention enhance delivery of perfume to fabrics and that preferred thermal treatment of the carrier comprises heating the carrier at a temperature between 500° C. and 700° C. for up to 2 hours.

Example 5

The effectiveness of hydrophobic silica for delivering perfume from standard and concentrated washing powders was assessed. 100 g samples of detergent powders were assessed by panel testing (20 people) and perfume strengths scored by Magnitude Estimation. Standard powders (Persil) contained 0.2% LP927LL and powder concentrates (Radion Micro) contained 0.5% LP927LL perfume. The reference samples simply had perfume added to the powders and the samples thoroughly mixed before use. With the carrier systems, the perfume was mixed thoroughly into the porous solid and the mix allowed to stand overnight before being dispersed into the detergent powder. Perfume intensities were assessed soon after sample preparation.

| Powder | Carrier | Carrier/Perf. Ratio | Perf. Intensity Score |||
|---|---|---|---|---|---|
| Standard | none (ref) | — | 118 | | |
| " | Sorbsil | 6:1 | 44 | | |
| Concentrate | none (ref) | — | 149 | 126 | 120 |
| " | Gasil | 6:1 | 121 | | |
| " | Sorbsil | 6:1 | 88 | | |
| " | Gasil | 5:1 | 110 | | |
| " | Sorbsil | 5:1 | 75 | | |
| " | Gasil | 4:1 | | 109 | |
| " | Sorbsil | 4:1 | | 66 | |

The results show lower perfume intensities for the powders containing microporous carriers at carrier/perfume ratios from 6:1 to 4:1.

The intensity of perfume delivered to an aqueous wash liquor was determined. The results for a standard powder formulation are given below.

| Powder | Carrier | Carrier/Perfume Ratio | Perfume Intensity Score |||
|---|---|---|---|---|---|
| Standard | none (ref) | — | 119 | 92 | 83 |
| " | Gasil | 6:1 | 85 | — | — |
| " | Sorbsil | 6:1 | 50 | 67 | 55 |
| " | (unperfumed) | — | 28 | | |

The results show that perfume intensities over wash liquours with hydrophobic carriers are lower than with the reference samples.

The example was repeated with the Radion Micro powder concentrate. In this test, 1.33 g of detergent powder concentrate (Radion Micro, freshly prepared with perfume or perfume/carrier) was weighed into a 1 litre glass jar, 500 ml tap water at 20° C. added, the jar sealed and the mixture shaken at intervals over the next 10/15 minutes. During the subsequent 15 minutes, a small panel (10 people) was then asked to rank the perfume strengths over the liquors.

Three samples (ref., hydrophilic and hyrophobic silica samples) were compared within half an hour of their preparation. The panel was asked to rank the samples in order of their perfume strength. The results were as follows:

| | | PERFUME RANKING (No. People) |||
|---|---|---|---|---|
| | Sample | Weakest | Intermediate | Strongest |
| 1) | hydrophilic Gasil | — | 2 | 8 |
| | reference with perfume directly added | 2 | 5 | 3 |
| | hydrophobic Gasil | 8 | 1 | 1 |
| 2) | reference with perfume directly added | 1 | 2 | 7 |
| | hydrophilic Sorbsil | 1 | 6 | 3 |
| | hydrophobic Sorbsil | 9 | 1 | — |

The results show that the hydrophobic carriers reduce perfume intensities of the wash liquors.

To determine the effectiveness of perfume delivery to the washed fabric Terry cotton was treated in a Tergotometer with 2.66 g detergent concentrate in 1 litre tap water at 45° C. for 15 minutes, rinsed in 1 litre water at room temperature for 5 minutes, squeezed out and line dried over night. Perfume intensities over the dry fabric were assessed by panels of 20 people using a 0–5 scale.

| Powder | Carrier | Carrier/Perfume Ratio | Perfume Intensity Score ||
|---|---|---|---|---|
| Concentrate | none (ref) | — | 0.70 | 0.64 |
| " | Gasil | 6:1 | 1.25 | 1.35 |
| " | Sorbsil | 6:1 | 1.80 | 1.83 |

This clearly demonstrates that hydrophobic carriers deliver enhanced levels of perfume to washed fabric from a concentrated detergent washing powder formulation.

Example 6

The effectiveness of hydrophobic perfume carriers according to the invention was assessed in a number of various washing powder formulations.

| Powders employed :- | |
|---|---|
| A) | high anionic powder - 17.6% LAS, 4.3% soap, 2.9% nonionic (STP/carbonate) |
| B) | high nonionic powder - 22.2% nonionic (zeolite/carbonate) |
| C) | high nonionic powder :- 2.8% PAS, 25.16% nonionic (zeolite) |
| D) | high nonionic powder :- 1.9% PAS, 17.5% nonionic (zeolite/carbonate/bleach) |
| E) | Radion Micro (as reference) - 6.26% LAS, 1.7% soap, 9.77% nonionic (zeolite/carbonate/bleach) |

Perfume intensities were assessed soon after sample preparation. The assessment was by panel testing—panels of about 20 people scoring the perfume strength on a 1–13 point scale.

Two hydrophobic silica carriers were used, Sorbsil and Gasil 200. The mean perfume intensity scores are shown below, All powders used the perfume LP927LL from Quest International at the ratio of 6:1 (silica:perfume) and with a perfume level of 0.6%.

| Powder | Carrier | Mean Perfume Intensity Score | | | | |
|---|---|---|---|---|---|---|
| | | 1 | 2 | 3 | 4 | 5 |
| A-high anionic | — | — | — | — | — | 8.14 |
| B-high nonionic | — | — | — | — | 6.68 | — |
| C-high nonionic | — | 7.79 | — | 7.63 | — | — |
| D-hich nonionic | — | 8.45 | — | — | — | — |
| E-Radion Micro | — | 8.75 | 7.81 | 7.41 | 7.04 | — |
| A-high anionic | Gasil | — | — | — | — | 7.57 |
| A-high anionic | Sorbsil | — | — | — | — | 3.28 |
| B-high nonionic | Sorbsil | — | — | — | 5.25 | — |
| C-high nonionic | Sorbsil | 6.45 | — | 5.91 | — | — |
| D-high nonionic | Gasil | — | 6.14 | — | — | — |
| D-high nonionic | Sorbsil | 5.41 | 5.95 | — | — | — |
| E-Radion Micro | Sorbsil | 6.00 | — | 6.04 | — | — |

The delivery of perfume to a fabric was determined. All powders samples contained 0.6% LP927LL. Thermally hydrophobed silica carriers were used throughout. Silica/perfume ratios were all at 6:1. Terry cotton was given a standard wash/rinse/line dry treatment and the perfume intensity assessed by panel testing after the fabric had dried overnight. Panels of about 20 people scored perfume intensity on a 0–5 scale.

| Powder | Carrier | Wash Liquor Conc. (g/L) | Mean Perfume Score | | |
|---|---|---|---|---|---|
| | | | 1 | 2 | 3 |
| A-high anionic | Sorbsil | 5 | — | — | 2.24 |
| A-high anionic | Gasil | 5 | — | — | 0.91 |
| B-high nonionic | Sorbsil | 5 | — | 2.95 | — |
| C-high nonionic | Sorbsil | 3 | 1.11 | — | — |
| D-high nonionic | Sorbsil | 5 | 2.01 | 1.48 | 1.07 |
| D-high nonionic | Gasil | 5 | 1.96 | 1.04 | — |
| D-high nonionic | Sorbsil | 3 | 1.32 | — | — |
| E-Radion Micro | Sorbsil | 5 | — | 0.98 | — |
| A-high anionic | — | 5 | — | — | 0.42 |
| B-high nonionic | — | 5 | — | 0.44 | — |
| C-high nonionic | — | 5 | 0.34 | — | — |
| D-high nonionic | — | 5 | 0.36 | — | — |
| E-Radion Micro | — | 3 | — | — | 0.42 |

In can be seen that the mean score for powders with carriers is higher than that for powders with perfume applied without a carrier. Thus showing enhanced delivery to the fabric.

Example 7

This example shows the delivery of perfume from a non-aqueous liquid detergent.
The liquid was unperfumed and comprised:
50% nonionic
6% ABS
17% Na carbonate
6% Ca carbonate
10.5% Na perborate plus odds & sods to 100% perfume level would be 0.5%
Perfume (LP927LL) (with and without silica carriers) was incorporated into the above at 0.5%.
100 ml samples were prepared and used to gauge perfume intensity over the liquids (panel test) on a 0–13 point scale. 1 ml samples were taken from these for examination by GC headspace analysis. Samples were also removed for use in our perfume delivery test (standard Tergotometer wash/rinse/line dry regime: wash liquour conc. was 2.4 g/L). The results detailed below are from freshly prepared samples.

| | PERFUME INTENSITY OVER LIQUIDS & GC HEADSPACE DATA. | | | |
|---|---|---|---|---|
| Silica Carrier | Mean Score | GC Headspace Peak Areas | | |
| | | % Due To Perfume | % Due To Nonionic | Total No GC Units |
| NONE (control) | 6.76 | 15.7 | 83.8 | 141164 |
| hydrophobic Sorbsil | 5.57 | 7.7 | 91.0 | 123843 |
| hydrophobic Gasil | 5.38 | 9.5 | 89.2 | 134134 |

PERFUME DELIVERY TO TERRY COTTON

Dry cloth were assessed for perfume intensity on a 0–5 point scale.

| Silica Carrier | Mean Fabric Score |
|---|---|
| hydrophobic Sorbsil | 2.98 |
| hydrophobic Gasil | 2.06 |
| NONE (control) | 0.18 |

Example 8

To show that vapour pressure could be reduced by use of non-silica hydrophobic materials, tests were conducted on Alumina and Magnesium Silicate particles with porosities falling within the range according to the present invention and morphologies fairly similar to those of silicas having the required porosity characteristics. The Alumina used was Pural SCC-5 ex Condea Chemie and the Magnesium Silicate was Magnesium Silicate M15 from Crosfield. SCC-5 has $V_b=0.0$ and $V_a=0.2$. M15 has $V_b=0.17$ and $V_a=0.10$.

By using 25 ml IPA in the hydrophobicity test to get wetting the percentage citral recovered was as shown below:

| Particle | % Citral recovery |
|---|---|
| SCC-5 | 2.8 |
| M15 | 43.0 |

It can be seen that the recovery for the alumina is low. This is due to poor wetting.

The particles were incorporated into a Persil washing powder formulation such that the perfume and carrier together comprised 0.2% of the total composition. Terry cloths were washed as described in Example 5. The perfume intensity on the cloth relative to a perfumed 'Persil' reference was as follows.

| Carrier | Perfume Intensity on Cloth | | | |
|---|---|---|---|---|
| | 1 | 2 | 3 | 4 |
| SCC5 | 1.25 | 1.85 | | |
| M15  400/2 Hrs | | | 0.80 | |
| 540/2 Hrs | | | 0.66 | |
| feed | | | 0.64 | |
| 750/2 Hrs | | | 0.29 | |
| Reference | 0.33 | 0.35 | 0.57 | |

The different M15 samples were thermally hydrophobed according to different schedules. All treatments were for 2 hours, but the temperatures varied from 400° C. to 750° C. It can be seen that for all except the highest temperature treatment of M15 the perfume delivery detected was an improvement over the reference.

We claim:

1. A hydrophobic porous inorganic carrier particle having at least a pore volume of 0.1 ml/g consisting of pores with a diameter of 7 to 50 Å and having a perfume absorbed into said particle.

2. A hydrophobic carrier as claimed in claim 1 wherein the particle has at least a pore volume of 0.2 ml/g consisting of pores with a diameter of 7 to 50 Å and having a perfume absorbed into said particle.

3. A hydrophobic carrier as claimed in claim 1 wherein the particle has at least a pore volume of 0.1 ml/g consisting of pores with a diameter of 11 to 40 Å.

4. A hydrophobic carrier as claimed in claim 1 wherein the particle has a carrier to perfume ratio by weight of less than 25:1.

5. A hydrophobic carrier as claimed in claim 1 wherein the carrier comprises silica.

6. A detergent composition comprising at least one surfactant and from 0.1 to 60% by weight of hydrophobic porous inorganic carrier particles having a pore volume of at least 0.1 ml/g consisting of pores with a diameter of 7 to 50 Å and having a perfume absorbed into said particle.

7. A method of making a hydrophobic, porous inorganic carrier particle having at least a pore volume of 0.1 ml/g consisting of pores with a diameter of 7 to 50 Å and having a perfume absorbed into said particle comprising the steps of:
(i) heating a suitable inorganic carrier at a temperature of from 500° C. to 1000° C. for up to 3 hours; and
(ii) treating the carrier with perfume.

* * * * *